United States Patent

Schneider

(10) Patent No.: US 8,228,028 B2
(45) Date of Patent: Jul. 24, 2012

(54) SYSTEMS AND METHODS FOR COMPENSATING FOR LARGE MOVING OBJECTS IN MAGNETIC-TRACKING ENVIRONMENTS

(75) Inventor: Mark R. Schneider, Williston, VT (US)

(73) Assignee: Ascension Technology Corporation, Milton, VT (US)

( * ) Notice: Subject to any disclaimer, the term of this patent is extended or adjusted under 35 U.S.C. 154(b) by 431 days.

(21) Appl. No.: 12/631,471

(22) Filed: Dec. 4, 2009

(65) Prior Publication Data

US 2010/0082280 A1   Apr. 1, 2010

Related U.S. Application Data

(63) Continuation-in-part of application No. PCT/US2008/065263, filed on May 30, 2008.

(60) Provisional application No. 60/942,009, filed on Jun. 5, 2007.

(51) Int. Cl.
*H02J 7/00* (2006.01)
*G01R 33/00* (2006.01)
*G01R 33/02* (2006.01)
*G01B 7/14* (2006.01)

(52) U.S. Cl. .................. 320/108; 324/200; 324/207.13; 324/207.14; 324/207.15; 324/207.16

(58) Field of Classification Search .................. 320/108
See application file for complete search history.

(56) References Cited

U.S. PATENT DOCUMENTS

| 5,640,170 A | * | 6/1997 | Anderson ............... 343/895 |
| 5,650,719 A | * | 7/1997 | Moody et al. ............ 324/166 |
| 7,081,748 B2 | | 7/2006 | Jakab |
| 2006/0025668 A1 | | 2/2006 | Peterson et al. |

FOREIGN PATENT DOCUMENTS

WO   2008154183   12/2008

OTHER PUBLICATIONS

International Search Report and Written Opinion dated Dec. 31, 2008 with regard to related PCT/US2008/065263 filed May 30, 2008, Schneider.

* cited by examiner

*Primary Examiner* — Edward Tso
*Assistant Examiner* — Ahmed Omar
(74) *Attorney, Agent, or Firm* — Downs Rachlin Martin PLLC

(57) ABSTRACT

Methods for accurately tracking position and orientation of a magnetic-field sensor in a tracking volume when a large magnetic-field distorter is present in the tracking volume. In some of the methods, magnetic field data is collected from within the tracking volume both with and without the large magnetic-field distorter present in the tracking volume. This data is used to obtain correction information that is subsequently used during real-time operation of the magnetic-field sensor to correct the position and orientation solutions for the sensor for magnetic-field distortions caused by the presence of the large magnetic-field distorter in the tracking volume. Others of the methods involve modeling the large magnetic-field distorter using dipole and multipole modeling. Magnetic tracking systems for implementing the methods include hardware and software for carrying out the methods.

54 Claims, 10 Drawing Sheets

SYSTEMS AND METHODS FOR COMPENSATING FOR LARGE MOVING OBJECTS IN MAGNETIC-TRACKING ENVIRONMENTS

RELATED APPLICATION DATA

This application is a continuation-in-part of International Application No. PCT/US08/65263, filed May 30, 2008, and titled "Systems and Methods for Compensating for Large Moving Objects in Magnetic-Tracking Environments," that claims the benefit of priority of U.S. Provisional Patent Application Ser. No. 60/942,009, filed Jun. 5, 2007, and titled "Method Of Compensating For Large Moving Objects In Electromagnetic Tracking Environments." Each of these applications is incorporated by reference herein in its entirety.

FIELD OF THE INVENTION

The present invention generally relates to the field of magnetic-tracking. In particular, the present invention is directed to systems and methods for compensating for large moving objects in magnetic-tracking environments.

BACKGROUND

Image-guided surgical procedures typically require placing surgical instruments, for example, catheters, scopes, probes, needles, ultrasound, ablators, drills, therapy delivery, therapy measure, physiological measure, etc., at a particular place, often at a particular orientation as well. Guiding these instruments in real-time is typically with respect to pre-acquired images from an imaging device, such as a computed tomography (CT) device, magnetic resonance imaging (MRI) device, etc., that are aligned with the guidance device. Images can also be acquired during the surgical procedure to update and correct pre-planned procedures, thus ensuring the best results practicable.

One of the best ways of guiding surgical instruments, both internal and external to a body being operated upon, is to use magnetic tracking technology. Numerous U.S. patents disclose magnetic tracking technology. These technologies all rely on a means of generating magnetic fields, sensing magnetic fields, and computing the position and orientation (P&O) of a device using the sensed fields. A drawback of magnetic tracking technology is when a live imaging device, such as an X-ray image intensifier (a/k/a a "C-arm"), is used during the surgical procedure: the device causes significant inaccuracies in the determination of the P&O. This inaccuracy is caused by the distortion of the magnetic field due to the metallic components of the imaging device, which are not accounted for (adequately, or at all) by the magnetic tracking algorithm being used. Many attempts have been made to account for these inaccuracies and are disclosed in numerous U.S. patents.

SUMMARY OF THE DISCLOSURE

In one implementation, the present disclosure is directed to a method of magnetic tracking in a tracking volume in the presence of movable magnetic-field distorter. The method includes: generating a magnetic field capable of being sensed by a magnetic-field sensor when the magnetic-field sensor is located in the tracking volume; obtaining first magnetic-field data regarding the magnetic field via the magnetic-field sensor while the magnetic-field sensor is in the tracking volume; calculating, within a machine, position and orientation of the magnetic-field sensor as a function of the first magnetic-field data and a difference between a first set of data items and a second set of data items, wherein the first set of data items results from second magnetic-field data collected from the tracking volume when the movable magnetic-field distorter is present in the tracking volume, and the second set of data items results from third magnetic-field data collected from the tracking volume when the movable magnetic-field distorter is not present in the tracking volume; and outputting from the machine information that is a function of the position and orientation of the magnetic-field sensor.

In another implementation, the present disclosure is directed to a system for magnetic tracking in a tracking volume in the presence of movable magnetic-field distorter. The system includes: a magnetic-field sensor; a magnetic field generator for generating a magnetic field capable of being sensed by the magnetic-field sensor when the magnetic-field sensor is located in the tracking volume; and means for: collecting first magnetic-field data regarding the magnetic field via the magnetic-field sensor while the magnetic-field sensor is in the tracking volume; and calculating position and orientation of the magnetic-field sensor as a function of the first magnetic-field data and a difference between a first set of data items and a second set of data items, wherein the first set of data items results from second magnetic-field data collected from the tracking volume when the movable magnetic-field distorter is present in the tracking volume, and the second set of data items results from third magnetic-field data collected from the tracking volume when the movable magnetic-field distorter is not present in the tracking volume.

In still another implementation, the present disclosure is directed to a computer-readable medium containing computer-executable instructions for use in performing a method of magnetic tracking in a tracking volume in the presence of movable magnetic-field distorter. The computer-executable instructions include: a first set of computer-executable instructions for obtaining first magnetic-field data regarding the magnetic field via the magnetic-field sensor while the magnetic-field sensor is in the tracking volume; a second set of computer-executable instructions for calculating position and orientation of the magnetic-field sensor as a function of the first magnetic-field data and a difference between a first set of data items and a second set of data items, wherein the first set of data items results from second magnetic-field data collected from the tracking volume when the movable magnetic-field distorter is present in the tracking volume, and the second set of data items results from third magnetic-field data collected from the tracking volume when the movable magnetic-field distorter is not present in the tracking volume; and a third set of computer-executable instructions for outputting from a machine information that is a function of the position and orientation of the magnetic-field sensor.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

Figure 1:
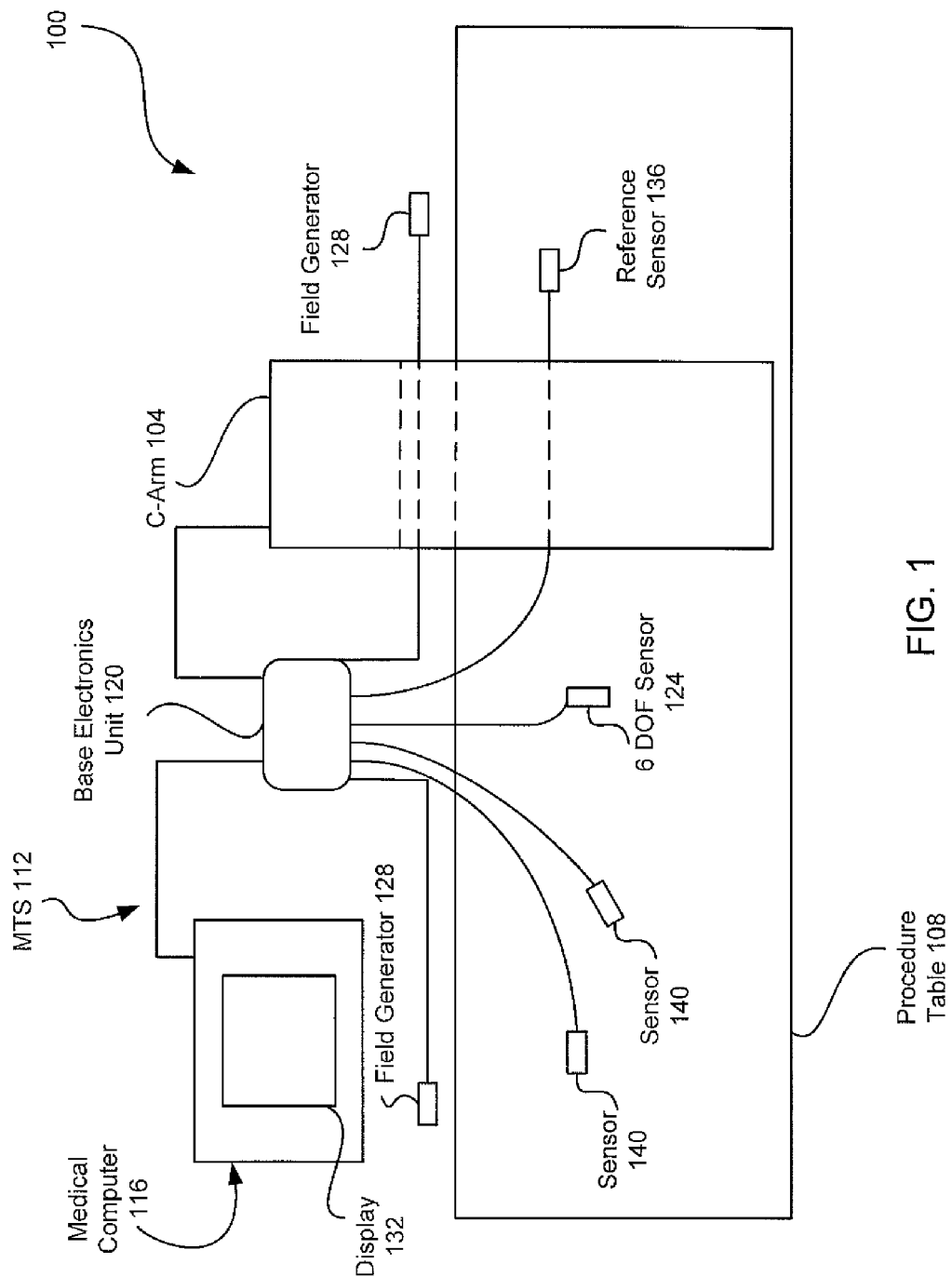
FIG. 1 is a schematic plan view of a surgical setting that includes a magnetic tracking system (MTS) that implements a method of improving the accuracy of the MTS.

This application discloses novel methods of improving the accuracy of magnetic tracking systems (MTSs) when in the presence of one or more large, movable objects. Referring now to the drawings, FIG. 1 illustrates an exemplary setting, here a surgical setting 100, in which any one of the novel methods of the present disclosure may be implemented. As those skilled in the art will readily appreciate, surgical setting 100 is but one example of settings in which a method of the present disclosure may be implemented and other settings will be recognizable to a skilled artisan. Other settings include helmet mounted sights used in both actual and simulated cockpits, VR applications (e.g., the CAVE), and labor and delivery assistive technology, to name a few. In this example, surgical setting 100 includes a C-arm 104, which constitutes the large, movable object mentioned above. Surgical setting 100 also includes a procedure table 108, an MTS 112 and a medical computer 116, among other things that are not particularly shown and are not necessary to describe the broad concepts and implementations of the present invention.

In this example, MTS 112 includes a base electronics unit 120, a six-degree-of-freedom (6DOF) sensor 124 and one or more magnetic field generators. In the present setup, a single magnetic field generator 128 is placed on the underside of procedure table 108. A patient is not shown for clarity. That said, those skilled in the art will understand that 6DOF sensor 124 may be located inside or outside the patient depending on the procedure being performed and/or the stage of the procedure and whether or not the patient is present. In one example, 6DOF sensor 124 and magnetic field generator 128 may be obtained from Ascension Technology Corporation, Milton, Vt. Base electronics unit 120 contains the circuitry and other components for providing the base functionality of MTS 112. MTS 112 is in communication with medical computer 116, which provides, among other things, the remaining functionality of the MTS, such as a graphical user interface and display. As those skilled in the art will readily appreciate, medical computer 116 may be a general purpose computer specially adapted for an operating room environment and may include one or more displays 132 for providing images, graphics and other visual information and/or graphical input functionality to medical personnel during use. In some cases, a reference sensor 136 may be used for correcting the accuracy of MTS 112, as described below. In other cases, one or more additional reference sensors 140 may be use for correcting the accuracy of MTS 112. Each of reference sensors 136, 140 may be any magnetic sensor suitable for this application and may be located inside or outside the patient depending on the procedure being performed and/or the stage of the procedure and whether or not the patient is present. Reference sensors do not need to be placed at "fixed" locations. While some applications benefit from having the reference sensor fixed, other applications may require the reference to move. Allowing the reference to move provides a means for negating the effects of respiratory, heart, or other patient movements on the tracked sensor (dynamic compensation). Measured movement of the reference sensor(s) can be subtracted from the tracked sensor(s) to achieve "quasi-stationary" tracked sensor measurements, free from motion artifact.

Figure 2A:
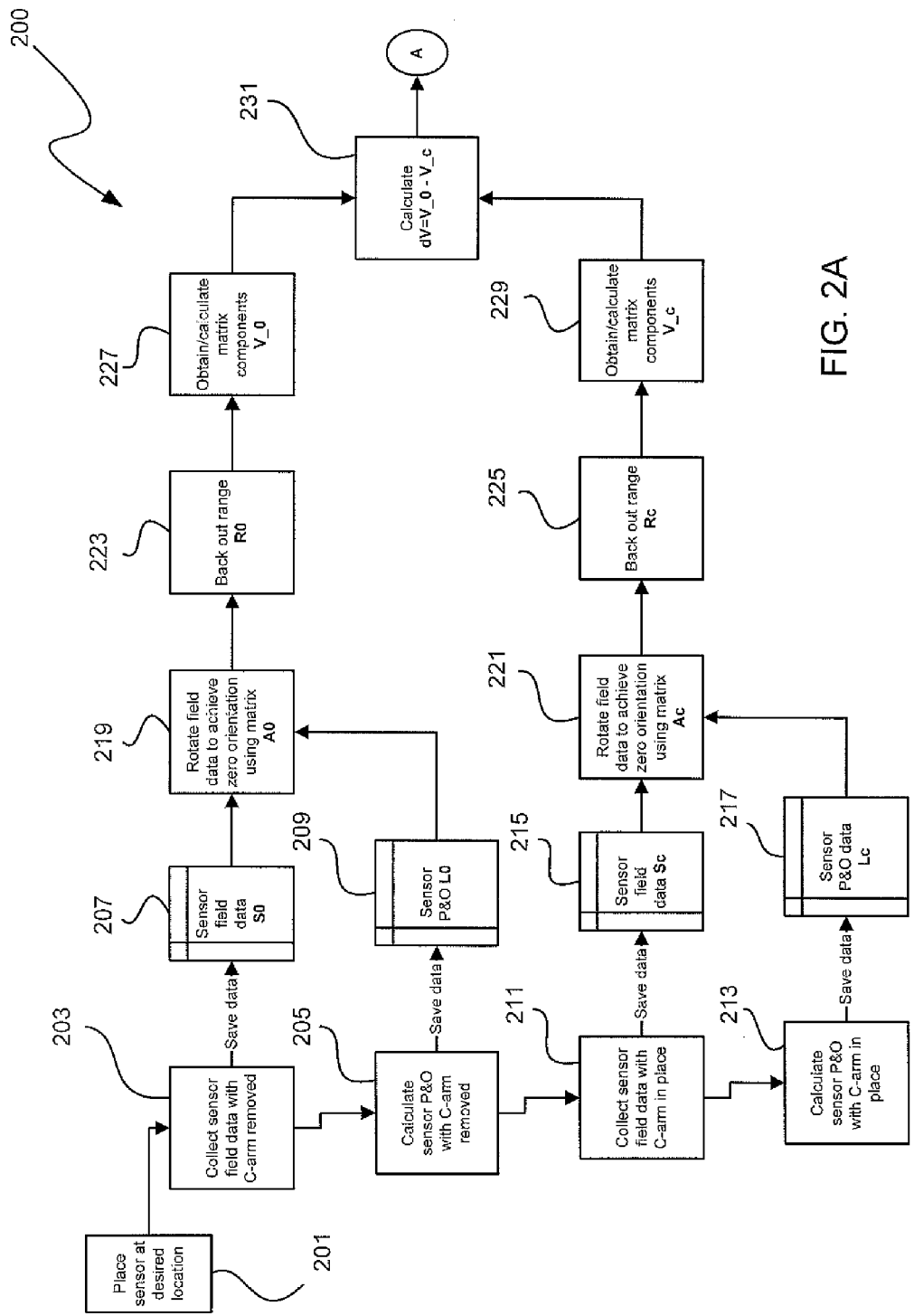
FIGS. 2A-B contain a flow diagram illustrating a method of improving accuracy of an MTS that can be used, for example, in the surgical setting of FIG. 1.
Figure 2B:
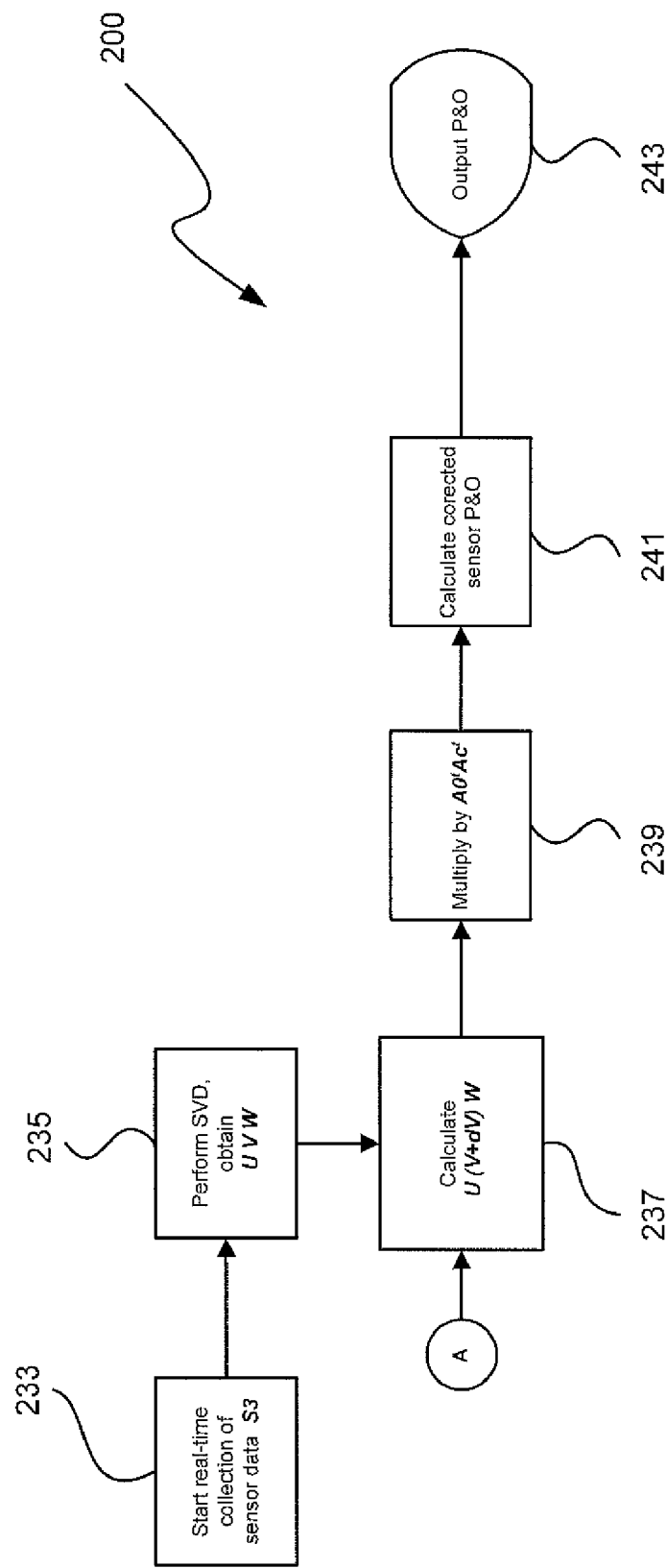

Referring now to FIGS. 2A-B, and also to FIG. 1, FIGS. 2A-B illustrate a method 200 of calculating corrected position and orientation (P&O) of a sensor in a setting that contains a large, movable object that may be moved during the time that P&O information is needed. For convenience, method 200 is described in the context of surgical setting 100 of FIG. 1. Consequently, the sensor under consideration is 6DOF sensor 124 and the large, movable object under consideration is C-arm 104. Those skilled in the art will understand that although method 200 is explained in the context of surgical setting 100 of FIG. 1, this method may indeed be used in other settings. At step 201, which is performed prior to performing the surgical procedure utilizing MTS 112, 6DOF sensor 124 is placed at or near a desired location, such as the location depicted in FIG. 1. This can be accomplished by the use of imaging available via C-arm 104, or not, and using tracking by MTS 112. After 6DOF sensor 124 is placed, C-arm 104 is withdrawn from surgical setting 100, and at steps 203 and 205, respectively, MTS 112 measures the fields at the sensor and calculates the P&O of the sensor. The sensed field data S0 and the calculated P&O L0 are saved at respective steps 207 and 209 for further processing. C-arm 104 is then brought back into surgical setting 100. 6DOF sensor 124 may be located inside or outside the patient depending on the procedure being performed and/or the stage of the procedure and whether or not the patient is present. Multiple measurements of the 6DOF sensor 124 may be obtained with and without the C-arm 104 in place but during patient movements to accomplish dynamic compensation.

After C-arm 104 has been brought back into surgical setting 100, at steps 211 and 213, respectively, new field measurements are collected using 6DOF sensor 124 and the P&O of the sensor is calculated. The sensed field data Sc and the calculated P&O Lc are saved at respective steps 215 and 217. It is noted that in the present example, the calculations may be performed by base electronics unit 120, medical computer 116 or a combination of both, depending on the setups of these components. Similarly, sensed field data S0, Sc and calculated P&O L0, Lc may be stored in base electronics unit 120, medical computer 116 or a combination of both.

At respective steps 219, 221 each set of field data S0, Sc is rotated to achieve zero orientation using corresponding matrices A0, Ac to rotate the fields. Each matrix A0, Ac is calculated from the corresponding respective orientation portion of P&O L0, Lc calculated at steps 205, 213, respectively, in a manner known in the art. These corrections are transformed into a zero sensor orientation reference frame so that they may be retransformed into any other orientation. Other methods may also be used to rotate the fields, and it may be advantageous to transform them into something other than a zero sensor orientation reference frame. At corresponding respective steps 223 and 225, ranges R0, Rc (as determined from steps 205, 213) are backed out of zero orientation matrices A0, Ac. Ranges R0, Rc can also be determined by other methods known in the art that are found in magnetic tracking algorithms and, in certain cases, may not need to be accounted for.

The resulting matrices contain information that can be extracted and used to provide corrections. This is represented in steps 227, 229 of method 200. In this example, the important properties calculated/obtained in steps 227, 229 are identified as components V_0, V_c of matrices V0, Vc, respectively and the difference between these matrices is used for correction of the distorting field. At step 231 the difference (dig) between matrices V0, Vc is calculated. Once this data is collected and saved, the run time collection of distorted field data can be started at step 233. In step 235, this data is also decomposed by singular value decomposition into three matrices. At this point, the V matrix is no longer ideal, so to correct it, the dV matrix is added to it at step 237. At step 239 orientation is then corrected by multiplying the result of step 237 by the $A0^{t} \cdot Ac^{t}$ (which also happens to equal the inverse of $A0 \cdot Ac$). At step 241a corrected P&O for 6DOF sensor 124 is calculated using the matrix resulting from step 239 by methods known in the art. The corrected P&O is output at step 243. It is noted that small displacements of 6DOF sensor 124 off from the original measurement will still benefit from this correction, but will degrade as the sensor is moved further away from its original measurement position. Small displacements may occur, for example, during respiration, mechanical heart motion, or other patient movements.

For a 5DOF sensor (not shown), only one vector need be measured. Therefore, corrections are only applicable if the sensor does not change position or orientation much from the original measurement. Measurements from 6DOF sensors, such as 6DOF sensor 124 of FIG. 1, can be used to correct both 6DOF and 5DOF sensors. Multiple 5DOF sensors, or measurements taken at various positions and orientations using 5DOF sensors, can also correct both 6DOF and 5DOF sensors.

Multiple sensor data sets (fields and P&O) can also be collected for use with method 200 of FIGS. 2A-B. While it is often preferable to collect the data sets with 6DOF sensors for maximum collection efficiency, 5DOF sensors can also be used. In certain applications, robotic instrumentation may place the sensors at known positions and orientations. In other applications, one or more surgical instruments, for example, catheters, probes, needles, etc., may place multiple sensors at multiple locations. The placement may be determined by an MTS, for example, MTS 112 of FIG. 1, when the large, movable object is removed from the sensor region, for example, when C-arm 104 is retracted, or may be determined by other means such as 2D fluoroscopy. While it is often preferred that all the data be collected from the multiple sensors in parallel, a single sensor may be translated and rotated throughout the area requiring compensation in order to build up a complete data set if needed. Single and multiple sensors may also be repositioned in space by repositioning the patient or taking advantage of patient movement artifact due to respiration, mechanical heart motion, etc.

At step 231 dV is typically calculated from an interpolated set of data. The same typically occurs at step 239, wherein the rotation matrices arise from an interpolated set of data. A minimum set of data for interpolation comes from at least four non-coplanar locations, with more data generally providing better results. Any number of methods may be used for the interpolation, depending on the data collected. This can be a polynomial fit, a spline, a table lookup, a Fourier or wavelet transform, the results from a partial differential equation solver, etc. Extrapolation can also be performed, but with worse results typical beyond the enclosed volume.

Figure 3:
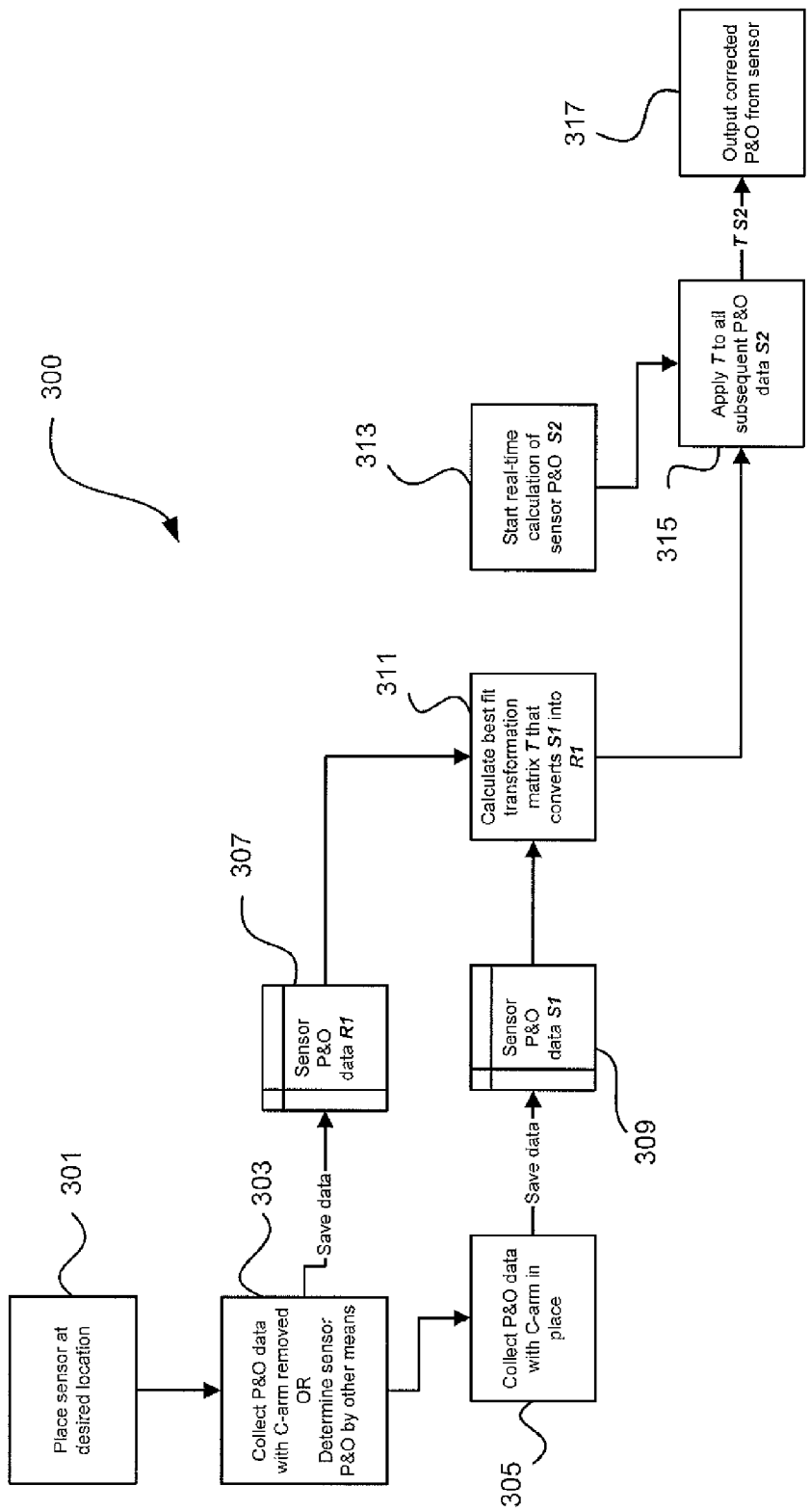
FIG. 3 is a flow diagram illustrating another method of improving accuracy of an MTS that can be used, for example, in the surgical setting of FIG. 1.

FIG. 3 illustrates a method 300 that can also be used to calculate corrected P&O of a sensor in a setting that contains a large, movable object that acts to distort magnetic fields in its vicinity. For convenience, method 300, like method 200, is described in the context of surgical setting of FIG. 1, with the understanding that this context is merely exemplary of different settings in which method 300 can be implemented. Those skilled in the art will readily understand how to adapt method 300 to the setting under consideration.

At a high level, instead of using field differences dV as in method 200 of FIGS. 2A-B, method 300 uses the P&O solutions before and after introducing C-arm 104 (FIG. 1) into surgical setting 100. As seen below, suitable rotation and translation are calculated to bring the P&O solution back to the original value (before introduction of C-arm 104). This transformation is used on all subsequent P&O calculations. This provides a purely relative measurement for localization. In many procedures, P&O of one sensor with respect to another sensor is all that is required for accurate localization of the second sensor. Sensors may be located inside or outside the patient depending on the procedure being performed and/or the stage of the procedure and whether or not the patient is present. Reference sensors do not need to be placed at "fixed" locations. While some applications benefit from having the reference sensor fixed, other applications may require the reference to move. Allowing the reference to move provides a means for negating the effects of respiratory, heart, or other patient movements on the tracked sensor (dynamic compensation). Measured movement of the reference sensor(s) can be subtracted from the tracked sensor(s) to achieve "quasi-stationary" tracked sensor measurements, free from motion artifact.

Referring now to FIG. 3, and also occasionally to FIG. 1, at step 301 reference sensor 136 is placed at a known location, for example, at an anatomical landmark (not shown). Such a known location can be determined using C-arm 104 or other means, such as ultrasound, if needed. At step 303, if C-arm 104 is present, the actual P&O data R1 for reference sensor 136 is determined by any suitable means other than MTS 112. However, if C-arm 104 is not present, MTS 112 can be used to determine actual P&O data R1 for reference sensor 136. At step 305, with the C-arm in the tracking volume, actual data is collected by MTS 112 and reference sensor 136, and the distorted P&O data S1 of the reference sensor is calculated. The two sets of P&O data R1, S1 for reference sensor 136 from steps 303 and 305 are stored, respectively, at steps 307 and 309.

Any distortion error will distort reference sensor 136 and the real-time tracked sensor(s), here 6DOF sensor 124, in a similar manner, allowing computing of the P&O of the tracked sensor(s) with respect to the reference sensor and suffer only a small error. To accomplish this, at step 311a best-fit transformation matrix T is calculated as between the actual P&O R1 of reference sensor 136 and the P&O solution S1 with or without C-arm 104. The transformation consists of a translation and a rotation. Calculating transformation matrix T can be accomplished in many ways, as is known in the art. After transformation matrix T has been calculated, real-time calculation of actual P&O data S2 for 6DOF sensor 124 can begin at step 313, for example, during an actual surgical procedure. At step 315 transformation matrix T from step 311 is then applied to the P&O data calculated from 6DOF sensor 124, with the corrected P&O solution being output at step 317. A simple version of method 300 is to use a fixed reference sensor (on or near the patient in this example) and calculate the P&O of the second sensor with respect to the fixed reference sensor. In this case, both the reference and real-time tracked sensors are subjected to almost the same distortion effects, so a simple subtraction removes the distortion effects. If the reference moves due to respiratory, heart, or other patient movements the measured movement of the reference sensor(s) can be subtracted from the tracked sensor(s) to achieve "quasi-stationary" tracked sensor measurements, free from motion artifact.

Figure 4:
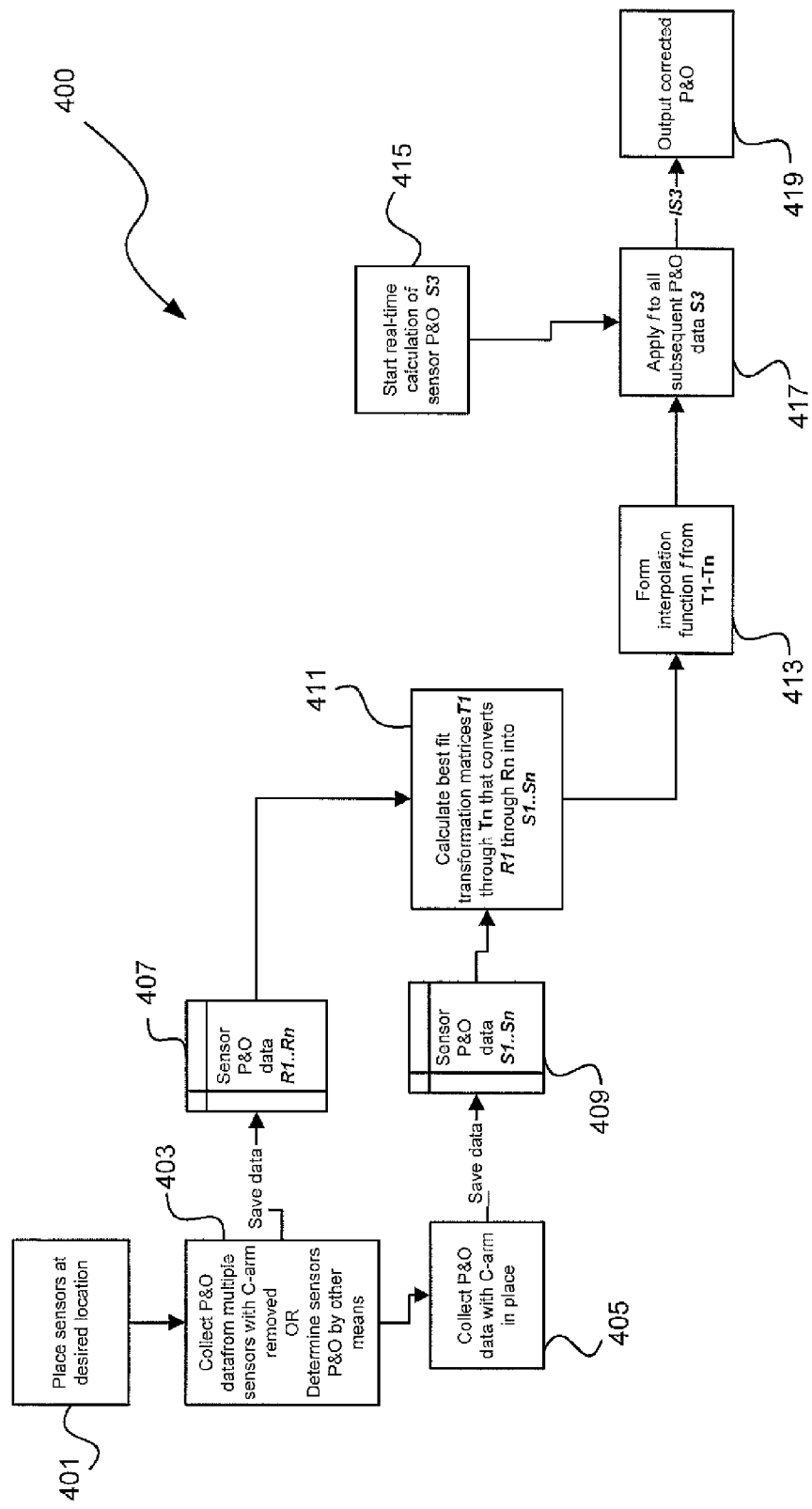
FIG. 4 is a flow diagram illustrating a further method of improving accuracy of an MTS that can be used, for example, in the surgical setting of FIG. 1.

FIG. 4 illustrates a method 400 that is based on method 300 of FIG. 3 and involves placing multiple reference sensors in the volume of interest at known locations. With these sensors all at known locations, interpolation methods are used to further increase the accuracy of the position determination of the tracked sensor, again with or without moving the large, movable object out of the tracking volume. A suitable rotation and translation are calculated to bring the P&O solutions of the reference sensors back to the original value (before introduction of the large, movable object). This transformation is used on all subsequent P&O calculations. This provides a purely relative measurement for localization. As mentioned above, in many procedures P&O of one sensor with respect to another sensor is all that is required for accurate localization of the second sensor. Sensors may be located inside or outside the patient depending on the procedure being performed and/or the stage of the procedure and whether or not the patient is present. If the reference sensors move due to respiratory, heart, or other patient movements the measured movement of the reference sensor(s) can be subtracted from the tracked sensor(s) to achieve "quasi-stationary" tracked sensor measurements, free from motion artifact.

Referring now to FIG. 4, and also occasionally to FIG. 1, at step 401 of method 400 reference sensors 136, 140 are placed at corresponding respective anatomical landmarks (not shown) or at other known locations. Such known locations can be determined using C-arm 104 or other means, such as ultrasound, if needed. At step 403, if C-arm 104 is present, the actual P&O data R1-Rn for reference sensors 136, 140 is determined by any suitable means other than MTS 112. However, if C-arm 104 is not present, MTS 112 can be used to determine actual P&O data R1-Rn for reference sensors 136, 140. At step 405, with the C-arm in the tracking volume, actual data is collected by MTS 112 and reference sensors 136, 140, and the distorted P&O data S1-Sn for the reference sensors is calculated. The two sets of P&O data R1-Rn, S1-Sn for reference sensors 136, 140 from steps 403 and 405 are stored, respectively, at steps 407 and 409.

Any distortion error will distort reference sensors 136, 140 and 6DOF sensor 124 in a similar manner, allowing computing of the P&O of the 6DOF sensor with respect to the reference sensors and suffer only a small error. To accomplish this, at step 411 best-fit transformation matrices T1-Tn are calculated that convert the actual P&Os R1-Rn of reference sensors 136, 140 into the P&O solution S1-Sn. Each transformation consists of a translation and a rotation. Calculating transformation matrices T1-Tn can be accomplished in many ways, as is known in the art. At step 413 an interpolation function $f$ is formed from transformation matrices T1-Tn. Function $f$ is interpolated and/or extrapolated to yield corrections within the volume defined by the space where the correction data was collected. A minimum set of data comes from at least four non-coplanar locations, with more data being better. Any number of methods may be used for the interpolation/extrapolation at step 413, depending on the data collected. This may be a polynomial fit, a spline, a table lookup, etc. The interpolation will be a function of position and orientation of the P&O calculated by each real-time tracked sensor. After function $f$ has been formed, real-time calculation of actual P&O data S3 for 6DOF sensor 124 can begin at step 415, for example, during an actual surgical procedure. At step 417 function $f$ from step 413 is then applied to the P&O data calculated from 6DOF sensor 124, with the corrected P&O solution being output at step 419.

Figure 5A:
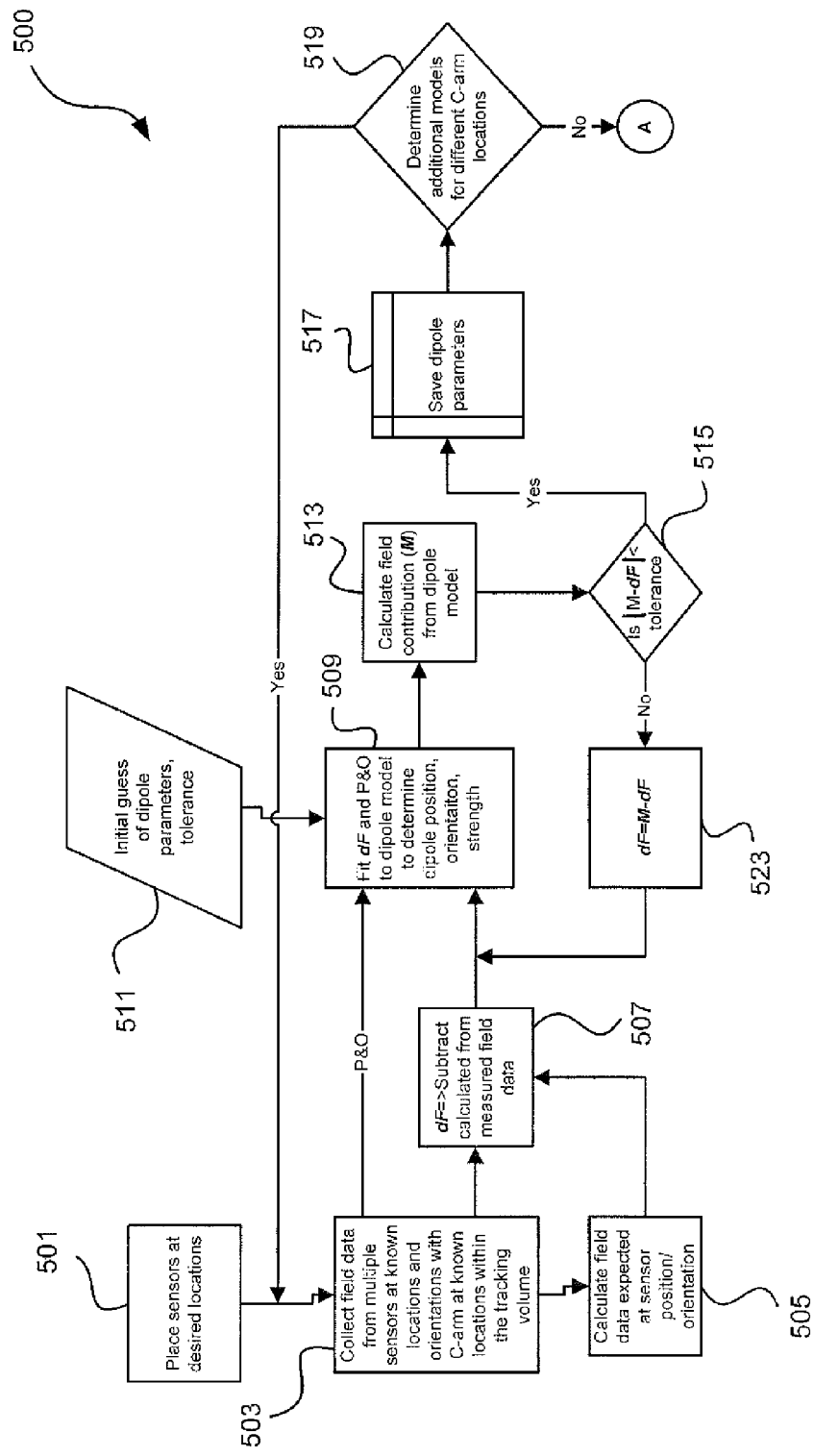
FIGS. 5A-B contain a flow diagram illustrating yet another method of improving accuracy of an MTS that can be used, for example, in the surgical setting of FIG. 1.
Figure 5B:
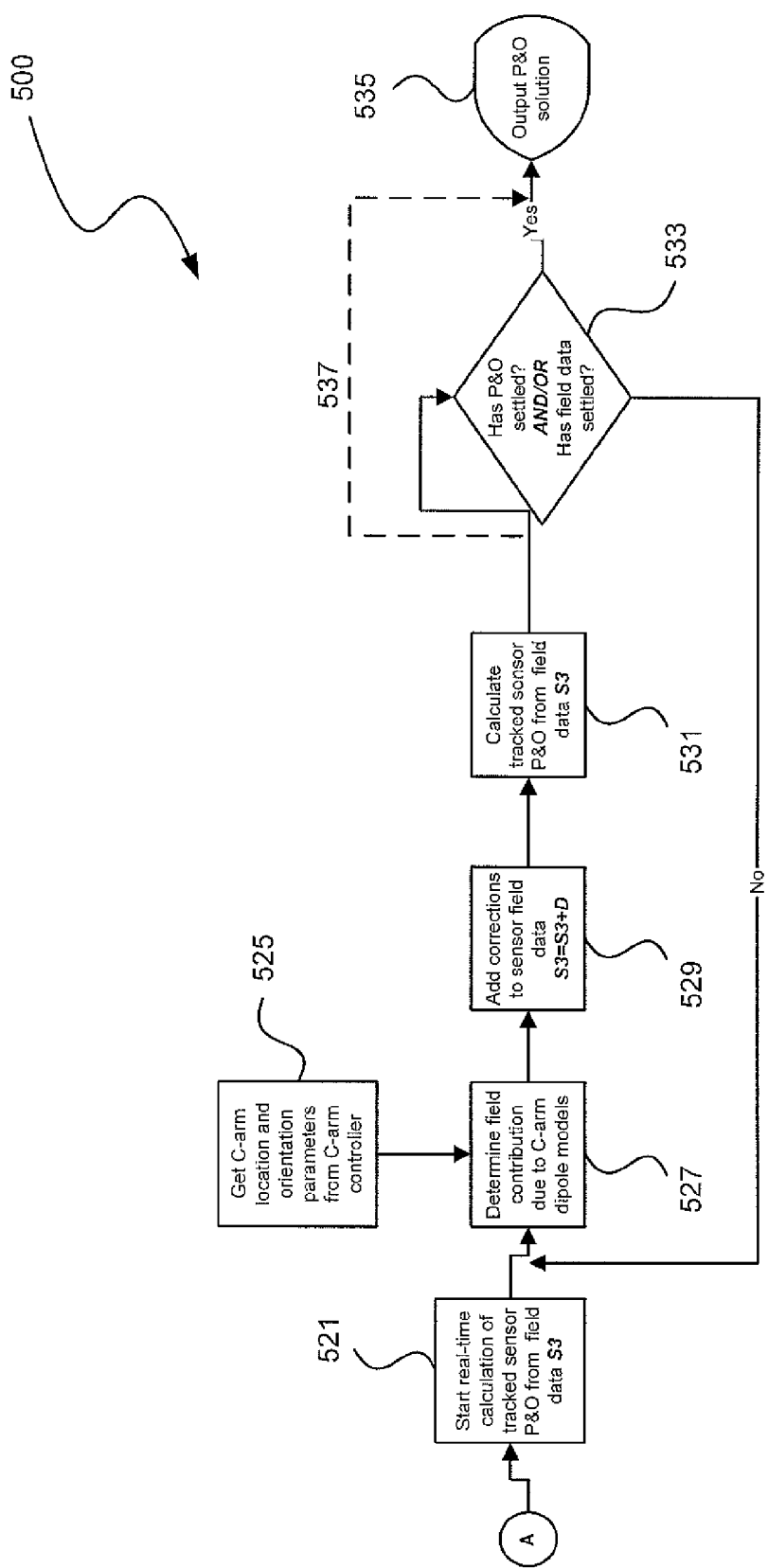

FIGS. 5A-B illustrate a method 500 that can be used to calculate corrected P&O of a sensor in a setting that contains a large, movable object that acts to distort magnetic fields in its vicinity. For convenience, method 500 is described in two parts: Part 1 (FIG. 5A) details an initialization stage, while Part 2 (FIG. 5B) describes use of data obtained in the initialization phase. At a high level, and as described below in more detail, field data collected from multiple sensors (or one sensor translated/rotated to multiple locations), is used to determine the position, orientation and strength of imaginary dipoles that can account for the distortion effects. A sufficient number of measurements are required to calculate this. For dipole fitting, the minimum number of data points is five, but more data provides a better fit. The fit can be determined using non-linear least squares techniques, Kalman filtering, or other known methods that allow the solution. Multiple dipoles can be fit if a sufficient quantity of field data is collected. Once the imaginary dipoles are calculated, their effects on the fields can be calculated for any position and orientation of a sensor within the tracking volume. Sensors may be located inside or outside the patient depending on the procedure being performed and/or the stage of the procedure and whether or not the patient is present. If the reference sensors move due to respiratory, heart, or other patient movements the measured movement of the reference sensor(s) can be subtracted from the tracked sensor(s) to achieve "quasi-stationary" tracked sensor measurements, free from motion artifact.

With that general overview in mind, attention is now directed to FIG. 5A, and also to FIG. 1. Again, surgical setting 100 of FIG. 1 is simply used for convenience to describe the broad concepts of method 500. In other words, the broad concepts of method 500 may be used in other settings. At step 501 in FIG. 5A multiple sensors, such as sensors 136, 140 (note that in this method sensors 136, 140 are not used as "reference" sensors in the same manner as discussed above relative to methods 200 and 300) are placed at known locations. At step 503 field data from sensors 124, 136, 140 is collected with C-arm 104 placed at a known location and orientation. (This can also be accomplished by placing a single sensor in multiple locations and collecting data in a serial manner.) Because sensors 124, 136, 140 are at known locations and orientations, at step 505 the field data expected at these places can be calculated. At step 507, the difference between the calculated field data and the measured field data is calculated and stored as a difference matrix dF. Using this difference matrix dF and the sensor placement and the C-arm placement from step 503, the parameters of a dipole model may be calculated at step 509 using an initial guess of dipole parameters and tolerance provided at step 511. The parameters calculated at step 509 can include a scale term (one parameter) and location and orientation terms (five parameters). More detailed models may contain additional parameters, as is known in the art. The method of determining the parameters includes non-linear least squares techniques, Kalman filtering, or other methods that allow the solution.

Once the dipole model parameters are calculated, at step 513 these parameters are plugged into the model to calculate the field contribution M based on the data collected in step 503. At step 515 field contributions M are compared against difference matrix dF. If the absolute difference between field contributions M and difference matrix dF is smaller than the user-supplied tolerance supplied at step 511, the parameters are saved off at step 517. At step 519, it is determined whether additional models are desired for other locations of C-arm 104. If so, C-arm 104 is moved to a new location and steps 503 through 519 are repeated to construct an additional model for different placements of C-arm 104. This process may be repeated to create models for all desired placements of C-arm 104. If no further models are desired at step 519, method 500 may continue to step 521 of Part 2 (FIG. 5B).

Referring to FIG. 5A, if at step 515 it is determined that the absolute difference between field contributions M and difference matrix dF is not smaller than the user-supplied tolerance supplied at step 511, at step 523 difference matrix dF is updated with the difference between field contributions M and difference matrix dF and method 500 re-enters step 509. An additional model is determined as before, and this process repeats until a sufficient number of models are determined to adequately fit the distortion from C-arm 104, as determined by the tolerance check at step 515. Again, tolerance is a user input that a user inputs at step 511 and is determined by how much error can be tolerated in the tracking algorithm.

After all the models and their parameters are determined in Part 1, the runtime dipole use of Part 2 (FIG. 5B) comes into play. At step 521 a real-time tracked sensor, here 6DOF sensor 124, is introduced and the P&O data for this sensor is calculated from its field data S3, and this field data is saved. At step 525, the location and orientation of C-arm 104 is identified by some mechanism, such as a controller (not shown) for the C-arm, as was used when the dipoles were modeled in Part 1. It is noted that if enough configurations of C-arm 104 are modeled, intermediate C-arm configurations can be interpolated to yield interpolated parameters to non-parameterized locations. At step 527, the contribution of the dipoles (D) is calculated based on the present P&O calculated at step 521. It is understood at the startup of this algorithm that the P&O is incorrect due to the fact that no modeled sources have yet been applied. The contributions to the fields are added (S3+D) at step 529. At step 531, this modified field data S3 is used to calculate a new P&O solution.

At optional step 533, it is determined whether the P&O solution of step 531 has settled and/or whether the modified field data S3 calculated at step 529 has settled. If a P&O solution that is settled to its final value is desired, step 533 compares the immediately previous P&O solution with the present one. If they are similar enough (last cycle's P&O solution approximately equal to the present cycles P&O and/or last cycle's field data S3 approximately equal to this cycle's field data S3), then the result is output at step 535. If they are not close enough, another iteration of correction is made by returning method 500 to step 527. In those situations where the corrections may never be good enough or timing is of a concern, a limitation on the number of branch backs can be provided, for example, by integrating a counter into step 533. In many applications, however, step 533 need not be used such that the P&O solution from step 531 is directly output at step 535, as indicated by dashed line 537. This will provide continuous output for every P&O solution. Once the P&O calculation settles after startup, real-time operation and correction tends to keep up because changes are based on incremental changes to the dipole D matrix.

Since motorized C-arms are common, data collected from known C-arm placements can be stored in a database (that, in the context of surgical setting 100 of FIG. 1, may reside in medical computer 116) to facilitate the distortion compensation. If the C-arm is placed at an already compensated location, the database is queried for the compensation data and applied forthwith. As noted, a C-arm can be modeled as one or more dipoles (also by differing dipoles at differing P&Os of the C-arm). This data can be collected once the C-arm is installed at a hospital, for example, and the dipole models can be stored as a function of C-arm position/orientation. Intermediate C-arm P&Os could be modeled by interpolating the predetermined dipole models. As a further enhancement, if C-arm P&O is not readily available, a fixed sensor in the tracking environment could monitor the distortion in the environment when the C-arm is positioned/oriented. This data, either distorted field data or distorted sensor P&O data, would then be mapped to the dipole models so that the correct model would be used.

One or more sensors can also be mounted to the field generator 128 or in the head of the C-arm, at known locations, to facilitate data collection. Sensors mounted in the transmitter are already at known, fixed positions and orientations. Sensors mounted on the C-arm need to be mounted in a known geometry. This sensor configuration would be characterized before installation on the C-arm. Once mounted, the distortion effect of the C-arm is measured and used to further refine the imaginary dipole calculations.

Other dipole determination methods are also disclosed in the literature and in patents. Some of these methods work in a similar manner, by first collecting field data from multiple sensors 503, fitting dipoles to data 509, calculating dipole contributions 513 and saving the dipole parameters for future use 517. For example, submarine warfare utilizes techniques for modeling submarines as dipoles. Magneto-encephalograms and certain cardiac electro-physiology applications also model various conditions using dipoles.

Figures 6A, 6B:
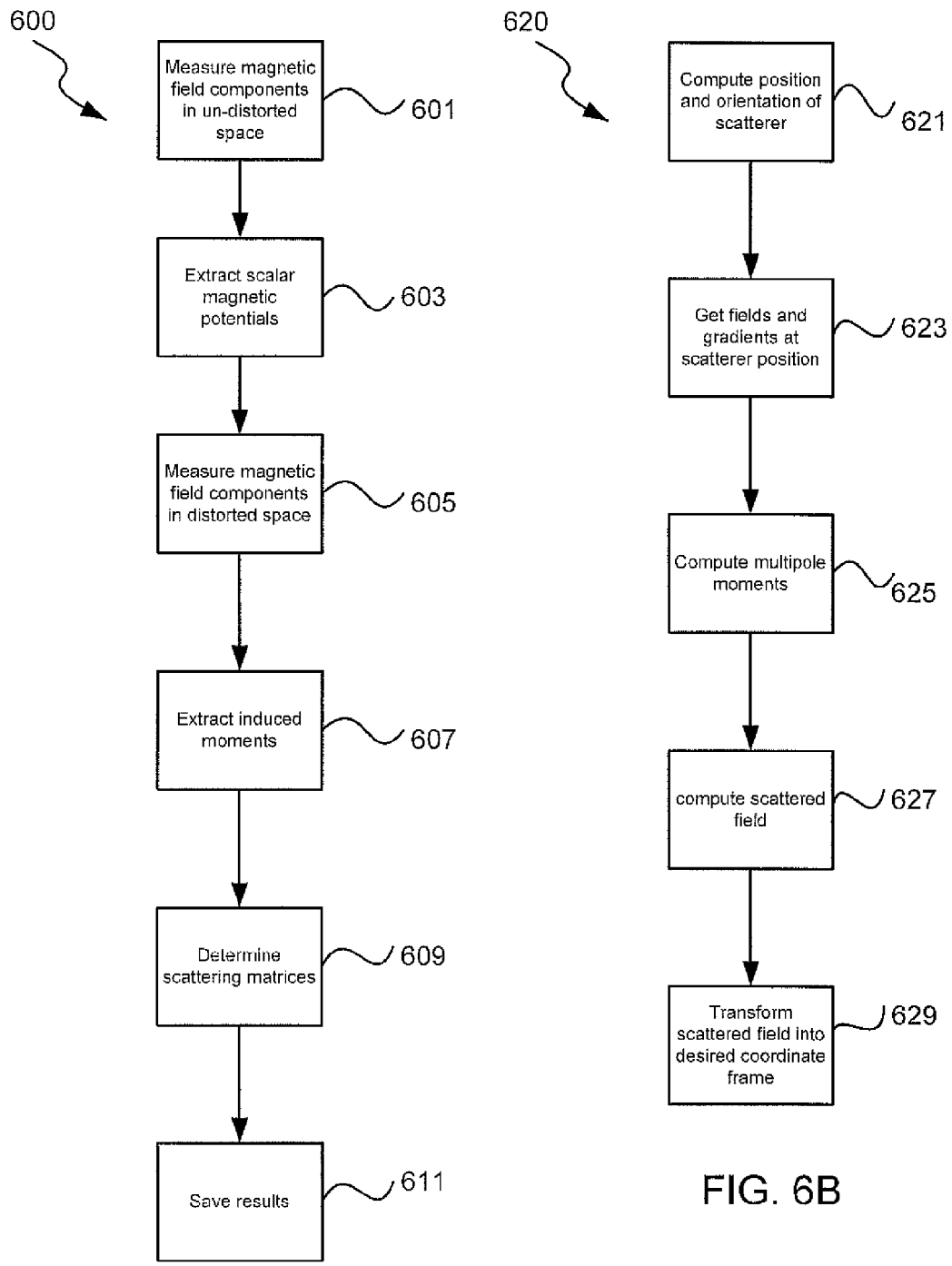
FIG. 6A is a flow diagram illustrating a characterization phase of a multipole-model-based method that can be used to improve the accuracy of an MTS.
FIG. 6B is a flow diagram illustrating a distortion compensation determination stage that may be used following the characterization phase of FIG. 6A.

FIGS. 6A-B are directed to portions of a method in which multipole fields are used to characterize the distorter, i.e., the large movable object (e.g., a C-arm). Discussions and methods directed to multipole modeling are disclosed in "Magnetic-Multipole Techniques for Moveable-Scatterer Compensation," Raab, F., and Brewster, C., Technical Report AAMRL-TR-88-054, November 1988, which is incorporated herein by reference in its entirety. Multipole moments are linearly related to the transmitted magnetic field and its gradients by a set of scattering coefficients. Scattering coefficients are determined from field measurements by applying, for example, linear coefficient fitting techniques.

Scalar magnetic potential theory is used to define a set of gradients that excite the multipole moments. Transformations for computing the distorting field from an arbitrarily positioned and oriented distorter (e.g., a C-arm) can be obtained by transforming the scalar magnetic potential gradients from one coordinate system to another. While it is preferred to have closed form solutions for the scatterer, mapping can be used to handle difficult, hard to characterize, gradients.

Referring to FIG. 6A, this figure details a characterization phase 600 wherein the distorter, for example, a movable imaging device such as C-arm 104 of FIG. 1, is characterized. At step 601 a field measurement sensor, for example 6DOF sensor 124 of FIG. 1, is moved about a tracking volume and magnetic field measurements are taken without the distorter present. Typically, this sensor would measure the three vector components from each of the positions in the volume of interest (i.e., the tracking volume). It is also possible to use multiple, single component measurements to build up this information.

The measurement data from step 601 is then curve fit at step 603 to extract the scalar magnetic potentials ($g_j$). These gradients are multidimensional partial derivatives of the measured magnetic fields. If the fields are not known, or not known well enough, then the gradients can be determined numerically. This can be accomplished when using polynomials or splines, which can be manipulated to determine derivatives, for example. This can be done by many methods known in the art, including polynomials, splines, rational functions, trigonometric functions, wavelets, to name a few. If a known function is available describing the fields and scatterer, then these are used directly instead of performing step 603.

The distorter is now introduced and, at step 605 the tracking volume is again mapped as was done at step 601. With this data available, at step 607 the induced moments ($p_k$) are extracted from the distorted data. Given $p_k$ and $g_j$, at step 609 the scattering matrices ($s_{k,j}$) are calculated from the following equation:

$$p_k = \sum_{j=1}^{J} s_{k,j} g_j(x, y, z)$$

This can be performed by methods known in the art, which include least squares methods for best fitting the scattering matrices to the data. The resulting matrices and gradients are saved at step 611. These results will be used in a distortion compensation determination phase 620 as detailed in FIG. 6B.

Referring to FIG. 6B, at step 621 the P&O of the scatterer (i.e., distorter, e.g., a C-arm) are determined. For this, the scatterer may be instrumented so that its P&O are noted and/or controlled with respect to the tracking volume. This can also be achieved with a dedicated sensor mounted on the scatterer that is in the tracking volume. After the P&O of the scatterer are known, at step 623 the gradients and scattering matrices saved at step 611 of FIG. 6A are evaluated at the position of the scatterer and rotated. At step 625 the rotated gradient and scattering matrices are then used to calculate the moments. At step 627 the scattered field components are then calculated, and at step 629 the field components are transformed into the desired tracking reference frame.

Figure 7:
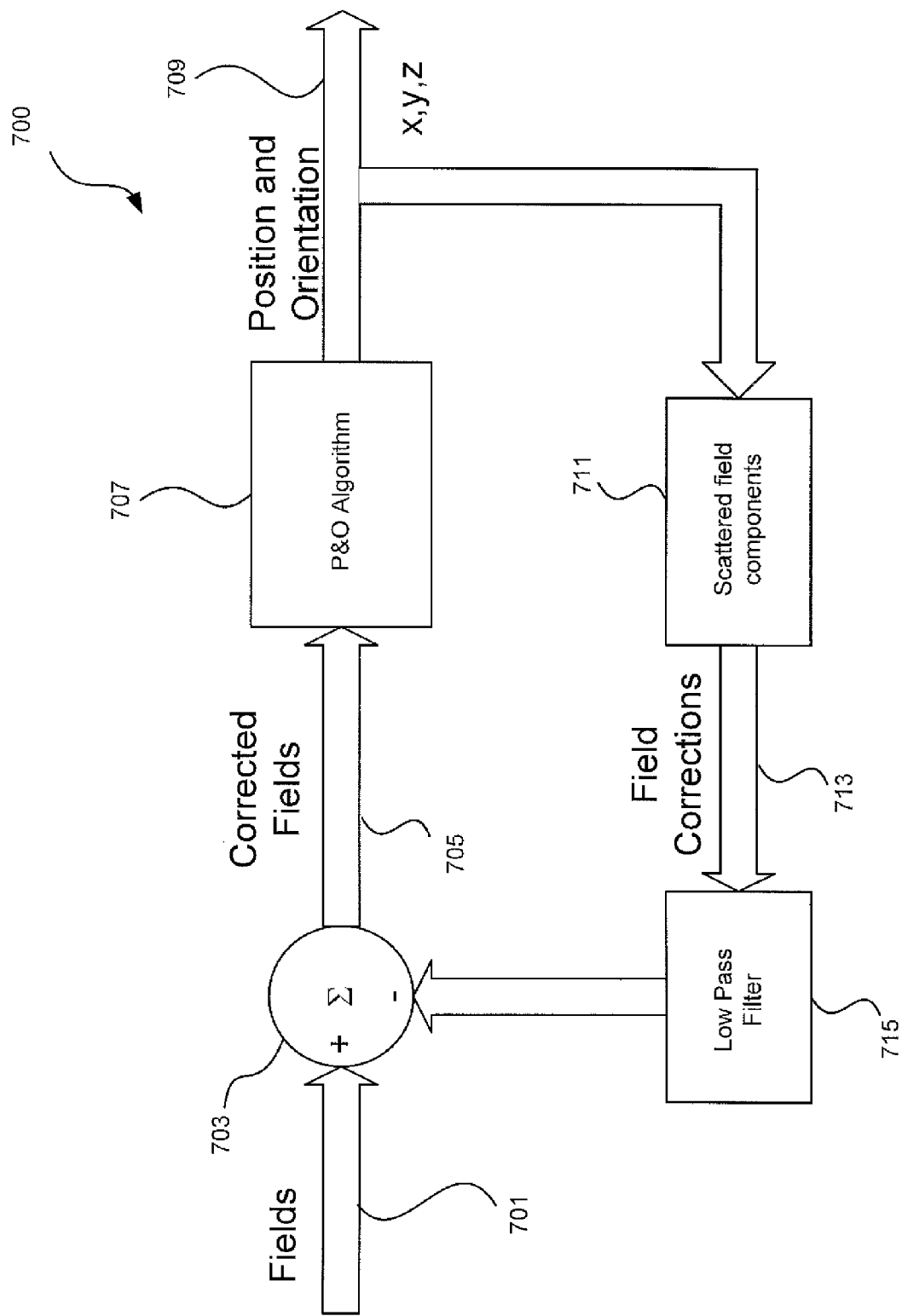
FIG. 7 is a flow diagram illustrating a real-time distortion compensation phase that may be used following the distortion compensation determination phase.

The scattered components calculated at step 627 are then used to correct for distortion as shown in FIG. 7, which details a method 700 of applying the distortion correction to an MTS. At step 701 field measurements are obtained from a sensor within the tracking volume discussed above relative to FIGS. 6A-B. The sensor may be located inside or outside the patient depending on the procedure being performed and/or the stage of the procedure and whether or not the patient is present. At the startup of method 700, no adjustments are available for the summation at step 703, and so the field measurements pass unchanged (i.e., initially, the corrected fields output at step 705 is equals to the field measurements input at step 701) through summation step 703. At step 707 the P&O of the sensor is calculated from the corrected fields at step 705 and is output to a user at step 709. The P&O algorithm used at step 707 may be any suitable algorithm known in the art. At step 711, the calculated P&O of step 709 is used to determine the scattered field components that effect it. At step 713 corrections are output from step 711. These corrections are then low pass filtered at step 715 to inhibit excessive changes between iterations, but this is not a necessity. At step 703 the filtered corrections are then added into the next field readings from step 701 and the process repeats.

In some embodiments, where distortion is at a minimum, or in the limiting case, non-existent, reference sensors may still be used to gain some advantage. As described above, reference sensors can compensate for patient or patient organ movement. This is true independent of the method of distortion compensation applied.

As will be readily understood by those skilled in the art, many steps of any one of methods 200, 300, 400, 500, 700 and phases 600, 620 may be performed by one or more computers, such as medical computer 116 of FIG. 1, and/or other machine(s), such as based electronics unit 120 of FIG. 1. Such computers and machines are typically microprocessor-based and can be programmed according to the teachings of the present specification, as will be apparent to those of ordinary skill in the computer arts. Appropriate software coding can readily be prepared by skilled programmers based on the teachings of the present disclosure, as will be apparent to those of ordinary skill in the software art.

Such software may be a computer program product that employs one or more machine-readable media and/or one or more machine-readable signals. A machine-readable medium may be any medium that is capable of storing and/or encoding a sequence of instructions for execution by a machine (e.g., a general purpose computing device) and that causes the machine to perform any one of the methodologies and/or embodiments described herein. Examples of a machine-readable medium include, but are not limited to, a magnetic disk (e.g., a conventional floppy disk, a hard drive disk), an optical disk (e.g., a compact disk "CD", such as a readable, writeable, and/or re-writable CD; a digital video disk "DVD", such as a readable, writeable, and/or rewritable DVD), a magneto-optical disk, a read-only memory "ROM" device, a random access memory "RAM" device, a magnetic card, an optical card, a solid-state memory device (e.g., a flash memory), an EPROM, an EEPROM, and any combination thereof. A machine-readable medium, as used herein, is intended to include a single medium as well as a collection of physically separate media, such as, for example, a collection of compact disks or one or more hard disk drives in combination with a computer memory.

Examples of a computing device include, but are not limited to, a computer workstation, a terminal computer, a server computer, a handheld device (e.g., tablet computer, a personal digital assistant "PDA", a mobile telephone, etc.), a web appliance, a network router, a network switch, a network bridge, a computerized device, such as a wireless sensor or dedicated proxy device, any machine capable of executing a sequence of instructions that specify an action to be taken by that machine, and any combination thereof. Medical devices, e.g., a C-arm, that are now digitally enhanced, could also include the computing device necessary to perform methods 200, 300, 400, 500, 700 and phases 600, 620.

Figure 8:
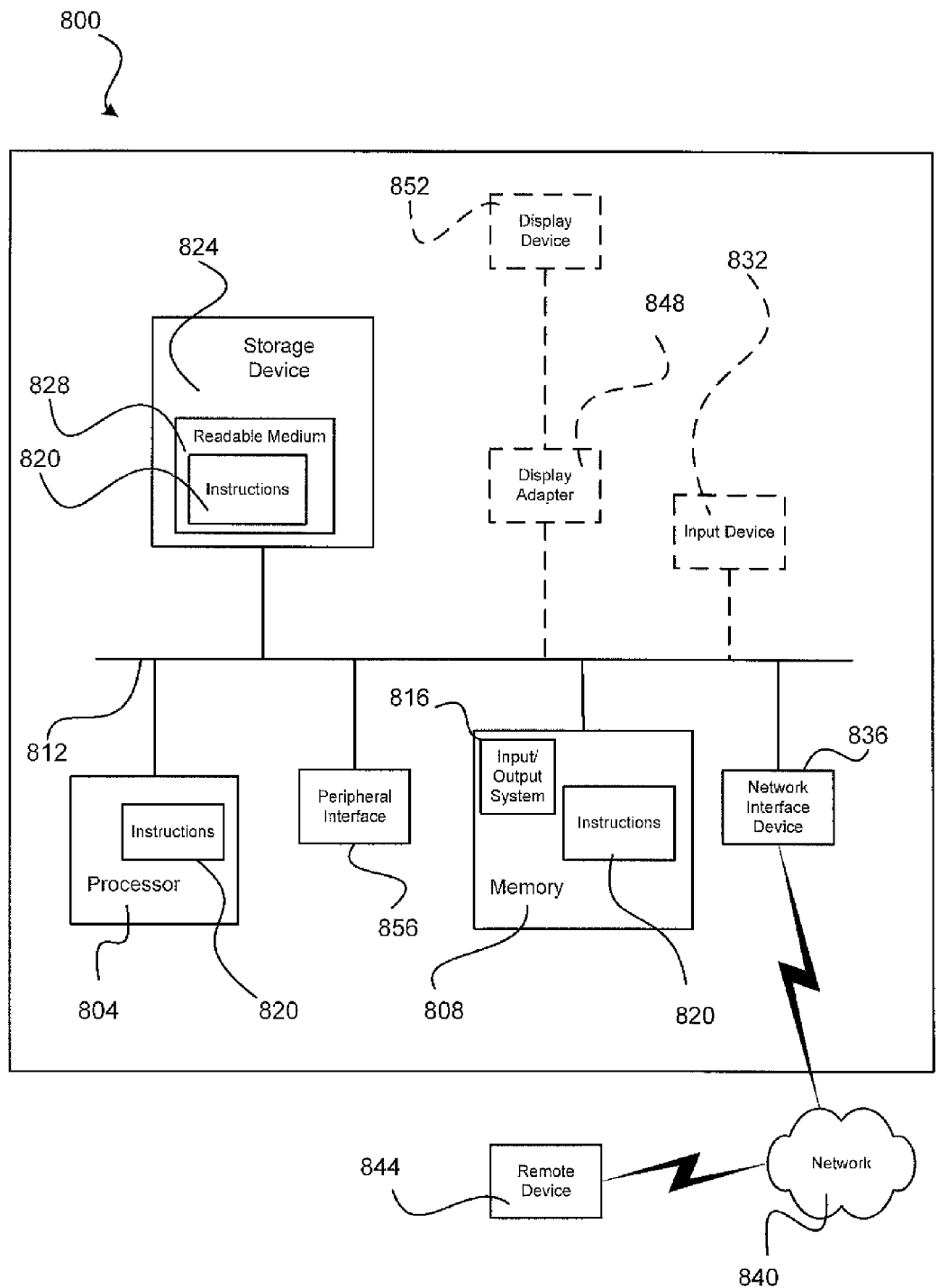
FIG. 8 is a block diagram of a computer system that may be used to implement a method of improving accuracy of an MTS.

FIG. 8 shows a diagrammatic representation of one embodiment of a computing device in the exemplary form of a computer system 800 within which a set of instructions for causing the device to perform any one or more of the aspects and/or methodologies of the present disclosure may be executed. Computer system 800 includes a processor 804 (e.g., a microprocessor or DSP) (more than one may be provided) and a memory 808 that communicate with each other, and with other components, via a bus 812. Bus 812 may include any of several types of bus structures including, but not limited to, a memory bus, a memory controller, a peripheral bus, a local bus, and any combination thereof, using any of a variety of bus architectures well known in the art.

Memory 808 may include various components including, but not limited to, a random access read/write memory component (e.g, a static RAM (SRAM), a dynamic RAM (DRAM), etc.), a read only component, and any combination thereof. In one example, a basic input/output system 816

(BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of instruction sets including, but not limited to, an operating system, one or more application programs, other program modules, program data, and any combination thereof.

Computer system 800 may also include one or more storage devices 824. Examples of storage devices suitable for use as any one of the storage devices 824 include, but are not limited to, a hard disk drive device that reads from and/or writes to a hard disk, a magnetic disk drive device that reads from and/or writes to a removable magnetic disk, an optical disk drive device that reads from and/or writes to an optical media (e.g., a CD, a DVD, etc.), a solid-state memory device, and any combination thereof. Each storage device 824 may be connected to bus 812 by an appropriate interface (not shown). Example interfaces include, but are not limited to, Small Computer Systems Interface (SCSI), advanced technology attachment (ATA), serial ATA, universal serial bus (USB), IEEE 13144 (FIREWIRE), and any combination thereof. In one example, storage device 824 may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data and/or data storage for computer system 800. In one example, software 820 may reside, completely or partially, within machine-readable medium 828. In another example, software 820 may reside, completely or partially, within processor 804.

In some embodiments, such as a general purpose computer, computer system 800 may also include one or more input devices 832. In one example, a user of computer system 800 may enter commands and/or other information into the computer system via one or more of the input devices 832. Examples of input devices that can be used as any one of input devices 832 include, but are not limited to, an alpha-numeric input device (e.g., a keyboard), a pointing device, a joystick, an audio input device (e.g., a microphone, a voice response system, etc.), a cursor control device (e.g., a mouse), a touchpad, an optical scanner, a video capture device (e.g., a still camera, a video camera), touchscreen, a digitizer pad, and any combination thereof. Each input device 832 may be interfaced to bus 812 via any of a variety of interfaces (not shown) including, but not limited to, a serial interface, a parallel interface, a game port, a Universal Serial Bus (USB) interface, a FIREWIRE interface, a direct interface to the bus, a wireless interface (e.g., a Bluetooth® connection) and any combination thereof.

Commands and/or other information may be input to computer system 800 via storage device 824 (e.g., a removable disk drive, a flash drive, etc.) and/or one or more network interface devices 836. A network interface device, such as network interface device 836, may be utilized for connecting computer system 800 to one or more of a variety of networks, such as network 840, and one or more remote devices 844 connected thereto. Examples of a network interface device include, but are not limited to, a network interface card, a modem, a wireless transceiver (e.g., a Bluetooth® transceiver) and any combination thereof. Examples of a network include, but are not limited to, a wide area network (e.g., the Internet, an enterprise network), a local area network (e.g., a network associated with an office, a building, a campus, a group of wireless sensors or other group of data streaming devices, or other relatively small geographic space), a telephone network, a direct connection between two computing devices, and any combination thereof. A network, such as network 840, may employ a wired and/or a wireless mode of communication. In general, any network topology may be used. Information (e.g., data, software 820, etc.) may be communicated to and/or from computer system 800 via the one or more network interface devices 836.

In some embodiments, such as a general purpose or medical computer, computer system 800 may further include a video display adapter 848 for communicating a displayable image to a display device, such as display device 852. Examples of a display device include, but are not limited to, a liquid crystal display (LCD), a cathode ray tube (CRT), a plasma display, and any combination thereof. In addition to a display device, a computer system 800 may include one or more other peripheral output devices including, but not limited to, an audio speaker, a printer, and any combination thereof. Such peripheral output devices may be connected to bus 812 via a peripheral interface 856. Examples of a peripheral interface include, but are not limited to, a serial port, a USB connection, a FIREWIRE connection, a parallel connection, and any combination thereof.

In some embodiments, computations and data storage may be distributed over multiple devices. Data relating to C-arm calibration, for example, might reside with the C-arm, while P&O calculations might occur in base electronics unit 120 and the corrections might occur in medical computer 116. The Digital Imaging and Communications in Medicine (DICOM) standard for distributing and viewing any kind of medical image regardless of the origin could also be used for enabling methods 200, 300, 400, 500, 700 and phases 600, 620, while integrating C-arm imaging.

A digitizer (not shown) and an accompanying pen/stylus, if needed, may be included in order to digitally capture freehand input. A pen digitizer may be separately configured or coextensive with a display area of display device 852. Accordingly, a digitizer may be integrated with display device 852, or may exist as a separate device overlaying or otherwise appended to the display device.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A method of magnetic tracking in a tracking volume in the presence of movable magnetic-field distorter, comprising:
   generating a magnetic field capable of being sensed by a magnetic-field sensor when the magnetic-field sensor is located in the tracking volume;
   obtaining first magnetic-field data regarding the magnetic field via the magnetic-field sensor while the magnetic-field sensor is in the tracking volume;
   calculating, within a machine, position and orientation of the magnetic-field sensor as a function of the first magnetic-field data and a difference between a first set of data items and a second set of data items, wherein the first set of data items results from second magnetic-field data collected from the tracking volume when the movable magnetic-field distorter is present in the tracking volume, and the second set of data items results from third magnetic-field data collected from the tracking volume when the movable magnetic-field distorter is not present in the tracking volume; and outputting from the machine information that is a function of the position and orientation of the magnetic-field sensor.

2. A method according to claim 1, wherein the data items of the first and second sets are position and orientation solutions calculated using a position-and-orientation algorithm.

3. A method according to claim 2, further comprising manipulating algorithmically the position and orientation solutions.

4. A method according to claim 1, wherein the data items of the first and second sets are magnetic-field measurements.

5. A method according to claim 4, further comprising manipulating algorithmically the magnetic-field measurements.

6. A method according to claim 1, further comprising interpolating the first and second sets of data items.

7. A method according to claim 1, wherein said calculating of position and orientation includes:
rotating the first magnetic-field data by a matrix A0 to obtain rotated first magnetic-field data having zero orientation;
rotating the second magnetic-field data by a matrix Ac to obtain zero orientation;
backing out a range R0 from the rotated first magnetic-field data;
backing out a range Rc from the rotated second magnetic-field data;
obtaining matrix components V0 from range R0;
obtaining matrix components Vc from range Rc;
determining a difference matrix dV between matrix components V0 and Vc;
collecting, via the magnetic-field sensor, real-time sensor field data;
obtaining matrix V from the real-time sensor data;
obtaining rebuilt sensor field data by incorporating the difference matrix dV into matrix V;
multiplying the rebuilt sensor field data by $A0^t Ac^t$ so as to obtain a corrected matrix;
calculating corrected position and orientation data for the magnetic-field sensor as a function of the corrected matrix; and
outputting from the machine information that is a function of the corrected position and orientation data.

8. A method according to claim 1, wherein said calculating of position and orientation includes:
determining, via the magnetic-field sensor with the magnetic-field distorter present in the tracking volume, position and orientation data R1 regarding the magnetic-field sensor at a particular location within the tracking volume;
determining, via the magnetic-field sensor with the magnetic-field distorter removed from the tracking volume, position and orientation data S1 regarding the magnetic-field sensor at the particular location;
calculating a best-fit transformation matrix T that converts S1 into R1;
collecting, via the magnetic-field sensor, real-time position and orientation data for location within the tracking volume;
applying the best-fit transformation matrix T to the real-time position and orientation data so as to obtain corrected position and orientation data; and
outputting from the machine information that is a function of the corrected position and orientation data.

9. A method according to claim 1, wherein said calculating of position and orientation includes:
determining, via at least one magnetic-field sensor with the magnetic-field distorter present in the tracking volume, position and orientation data sets R1 . . . Rn corresponding to differing locations of the at least one magnetic-field sensor within the tracking volume;
determining, via the at least one magnetic-field sensor with the magnetic-field distorter removed from the tracking volume, position and orientation data sets S1 . . . Sn corresponding to the differing locations;
calculating a best-fit transformation matrices T1 . . . Tn that convert corresponding respective ones of R1 . . . Rn into corresponding respective ones of S1 . . . Sn;
forming an interpolation function $f$ from best-fit transformation matrices T1 . . . Tn;
collecting, via the at least one magnetic-field sensor, real-time position and orientation data;
applying the interpolation function $f$ to the real-time position and orientation data so as to obtain corrected position and orientation data; and
outputting from the machine information that is a function of the corrected position and orientation data.

10. A method according to claim 1, wherein said calculating of position and orientation includes:
(a) collecting, with the magnetic-field distorter at a known distorter location within the tracking volume, measured magnetic-field data from one or more sensors placed at known sensor locations and orientations within the tracking volume;
(b) calculating expected magnetic-field data expected at each of the known sensor positions and orientations;
(c) determining a difference dF between the measured magnetic-field data and the expected magnetic-field data;
(d) fitting the difference dF and the measured positions and orientations to a dipole model so as to determine dipole parameters;
(e) calculating a magnetic-field contribution M from the dipole model;
(f) determining if |M−dF| is less than a tolerance; and
(g) if |M−dF| is less than the tolerance, save the dipole parameters.

11. A method according to claim 10, further comprising, if |M−dF| is not less than the tolerance:
(h) calculating a new dF=M−dF;
(i) repeating steps (d) through (h) using the new dF until |M−dF| is less than the tolerance.

12. A method according to claim 11, further comprising repeating steps (a) through (i) multiple times for differing distorter locations.

13. A method according to claim 10, further comprising:
(j) collecting real-time magnetic-field data S3 from the at least one magnetic-field sensor;
(k) obtaining real-time distorter location and orientation parameters;
(l) determining a dipole contribution D as a function of the real-time distorter location and orientation parameters;
(m) calculating corrected real-time magnetic-field data as a function of the real-time magnetic-field data S3 and the dipole contribution D;
(n) calculating corrected position and orientation using the corrected real-time magnetic-field data; and
(o) outputting from the machine information that is a function of the corrected position and orientation data.

14. A method according to claim 13, further comprising prior to step (o):
(p) determining if the corrected position and orientation data has settled and/or if the corrected real-time magnetic-field data has settled;
(q) if one, the other, or both, of the corrected position and orientation data has not settled and/or if the corrected real-time magnetic-field data has settled, repeating steps (l) through (n) and (p); and
(r) if one, the other, or both, of the corrected position and orientation data has settled and/or if the corrected real-time magnetic-field data has settled, proceeding to step (o).

15. A method according to claim 1, wherein said calculating of position and orientation includes:
measuring first magnetic-field components within the tracking volume without the magnetic-field distorter present in the tracking volume;
extracting scalar magnetic potentials $g_j$, from the first magnetic-field components;
measuring second magnetic-field components within the tracking volume with the magnetic-field distorter present in the tracking volume;
extracting induced moments $p_k$ from the second magnetic-field components;
determining gradient and scattering matrices $s_{k,j}$ from the scalar magnetic potentials and the induced moments $p_k$;
determine a distorter position and orientation of the magnetic-field distorter;
evaluating and rotating the gradient and scattering matrices as a function of the distorter position and orientation so as to obtain rotated gradient and scattering matrices;
computing multipole moments as a function of the rotated gradient and scattering matrices;
calculating a scattered field as a function of the multipole moments; and
transforming the scattered field to a desired coordinate frame so as to obtain transformed scattered field.

16. A method according to claim 15, further comprising:
(a) collecting real-time magnetic-field data from the magnetic-field sensor;
(b) summing the real-time magnetic-field data with a magnetic-field corrections so as to obtain corrected magnetic-field data;
(c) determining corrected real-time position and orientation data as a function of the corrected magnetic-field data;
(d) outputting information as a function of the corrected real-time position and orientation data;
(e) determining the magnetic-field corrections as a function of the transformed scattered field and the corrected real-time position and orientation data; and
(f) repeating steps (a) through (e).

17. A method according to claim 16, further comprising low-pass filtering the magnetic-field corrections prior to step (b).

18. A method according to claim 15, wherein said determining of the gradient and scattering matrices $s_{k,j}$ from the scalar magnetic potentials $g_j$, and the induced moments $p_k$ includes solving the following equation for $s_{k,j}$:

$$p_k = \sum_{j=1}^{J} s_{k,j} g_j(x, y, z).$$

19. A system for magnetic tracking in a tracking volume in the presence of movable magnetic-field distorter, comprising:
a magnetic-field sensor;
a magnetic field generator for generating a magnetic field capable of being sensed by said magnetic-field sensor when said magnetic-field sensor is located in the tracking volume; and
means for:
collecting first magnetic-field data regarding the magnetic field via said magnetic-field sensor while said magnetic-field sensor is in the tracking volume; and
calculating position and orientation, of said magnetic-field sensor as a function of the first magnetic-field data and a difference between a first set of data items and a second set of data items, wherein the first set of data items results from second magnetic-field data collected from the tracking volume when the movable magnetic-field distorter is present in the tracking volume, and the second set of data items results from third magnetic-field data collected from the tracking volume when the movable magnetic-field distorter is not present in the tracking volume.

20. A system according to claim 19, wherein the data items of the first and second sets are position and orientation solutions calculated using a position-and-orientation algorithm.

21. A system according to claim 20, wherein said means is further for manipulating algorithmically the position and orientation solutions.

22. A system according to claim 19, wherein the data items of the first and second sets are magnetic-field measurements.

23. A system according to claim 22, wherein said means is further for manipulating algorithmically the magnetic-field measurements.

24. A system according to claim 19, wherein said means is further for interpolating the first and second sets of data items.

25. A system according to claim 19, wherein said means is further for:
rotating the first magnetic-field data by a matrix A0 to obtain rotated first magnetic-field data having zero orientation;
rotating the second magnetic-field data by a matrix Ac to obtain zero orientation;
backing out a range R0 from the rotated first magnetic-field data;
backing out a range Rc from the rotated second magnetic-field data;
obtaining matrix components V0 from range R0;
obtaining matrix components Vc from range Rc;
determining a difference matrix dV between matrix components V0 and Vc;
collecting, via the magnetic-field sensor, real-time sensor field data;
obtaining matrix V from the real-time sensor data;
obtaining rebuilt sensor field data by incorporating the difference matrix dV into matrix V;
multiplying the rebuilt sensor field data by $A0^t Ac^t$ so as to obtain a corrected matrix;
calculating corrected position and orientation data for the magnetic-field sensor as a function of the corrected matrix; and
outputting from the machine information that is a function of the corrected position and orientation data.

26. A system according to claim 1, wherein said means is further for:
determining, via the magnetic-field sensor with the magnetic-field distorter present in the tracking volume, position and orientation data R1 regarding the magnetic-field sensor at a particular location within the tracking volume;

determining, via the magnetic-field sensor with the magnetic-field distorter removed from the tracking volume, position and orientation data S1 regarding the magnetic-field sensor at the particular location;

calculating a best-fit transformation matrix T that converts S1 into R1;

collecting, via the magnetic-field sensor, real-time position and orientation data for location within the tracking volume;

applying the best-fit transformation matrix T to the real-time position and orientation data so as to obtain corrected position and orientation data; and outputting from the machine information that is a function of the corrected position and orientation data.

27. A system according to claim 1, wherein said means is further for:

determining, via at least one magnetic-field sensor with the magnetic-field distorter present in the tracking volume, position and orientation data sets R1 . . . Rn corresponding to differing locations of the at least one magnetic-field sensor within the tracking volume;

determining, via the at least one magnetic-field sensor with the magnetic-field distorter removed from the tracking volume, position and orientation data sets S1 . . . Sn corresponding to the differing locations;

calculating a best-fit transformation matrices T1 . . . Tn that convert corresponding respective ones of R1 . . . Rn into corresponding respective ones of S1 . . . Sn;

forming an interpolation function $f$ from best-fit transformation matrices T1 . . . Tn;

collecting, via the at least one magnetic-field sensor, real-time position and orientation data;

applying the interpolation function $f$ to the real-time position and orientation data so as to obtain corrected position and orientation data; and outputting from the machine information that is a function of the corrected position and orientation data.

28. A system according to claim 1, wherein said means is further for:
(a) collecting, with the magnetic-field distorter at a known distorter location within the tracking volume, measured magnetic-field data from one or more sensors placed at known sensor locations and orientations within the tracking volume;
(b) calculating expected magnetic-field data expected at each of the known sensor positions and orientations;
(c) determining a difference dF between the measured magnetic-field data and the expected magnetic-field data;
(d) fitting the difference dF and the measured positions and orientations to a dipole model so as to determine dipole parameters;
(e) calculating a magnetic-field contribution M from the dipole model;
(f) determining if |M−dF| is less than a tolerance; and
(g) if |M−dF| is less than the tolerance, save the dipole parameters.

29. A system according to claim 10, wherein said means is further for, if |M−dF| is not less than the tolerance:
(h) calculating a new dF=M−dF;
(i) repeating functions (d) through (h) using the new dF until |M−dF| is less than the tolerance.

30. A system according to claim 11, wherein said means is further for repeating functions (a) through (i) multiple times for differing distorter locations.

31. A system according to claim 10, wherein said means is further for:
(j) collecting real-time magnetic-field data S3 from the at least one magnetic-field sensor;
(k) obtaining real-time distorter location and orientation parameters;
(l) determining a dipole contribution D as a function of the real-time distorter location and orientation parameters;
(m) calculating corrected real-time magnetic-field data as a function of the real-time magnetic-field data S3 and the dipole contribution D;
(n) calculating corrected position and orientation using the corrected real-time magnetic-field data; and
(o) outputting from the machine information that is a function of the corrected position and orientation data.

32. A system according to claim 13, wherein said means is further for, prior to function (o):
(p) determining if the corrected position and orientation data has settled and/or if the corrected real-time magnetic-field data has settled;
(q) if one, the other, or both, of the corrected position and orientation data has not settled and/or if the corrected real-time magnetic-field data has settled, repeating functions (l) through (n) and (p); and
(r) if one, the other, or both, of the corrected position and orientation data has settled and/or if the corrected real-time magnetic-field data has settled, proceeding to function (o).

33. A system according to claim 1, wherein said means is further for:

measuring first magnetic-field components within the tracking volume without the magnetic-field distorter present in the tracking volume;

extracting scalar magnetic potentials $g_j$, from the first magnetic-field components;

measuring second magnetic-field components within the tracking volume with the magnetic-field distorter present in the tracking volume;

extracting induced moments $p_k$ from the second magnetic-field components;

determining gradient and scattering matrices $s_{k,j}$ from the scalar magnetic potentials $g_j$, and the induced moments $p_k$;

determine a distorter position and orientation of the magnetic-field distorter;

evaluating and rotating the gradient and scattering matrices as a function of the distorter position and orientation so as to obtain rotated gradient and scattering matrices;

computing multipole moments as a function of the rotated gradient and scattering matrices;

calculating a scattered field as a function of the multipole moments; and transforming the scattered field to a desired coordinate frame so as to obtain transformed scattered field.

34. A system according to claim 15, wherein said means is further for:
(a) collecting real-time magnetic-field data from the magnetic-field sensor;
(b) summing the real-time magnetic-field data with a magnetic-field corrections so as to obtain corrected magnetic-field data;
(c) determining corrected real-time position and orientation data as a function of the corrected magnetic-field data;

(d) outputting information as a function of the corrected real-time position and orientation data;
(e) determining the magnetic-field corrections as a function of the transformed scattered field and the corrected real-time position and orientation data; and
(f) repeating functions (a) through (e).

35. A system according to claim 16, wherein said means is further for low-pass filtering the magnetic-field corrections prior to function (b).

36. A system according to claim 15, wherein said means is further for determining the gradient and scattering matrices $s_{k,j}$ from the scalar magnetic potentials $g_j$, and the induced moments $p_k$ by solving the following equation for $s_{k,j}$:

$$p_k = \sum_{j=1}^{J} s_{k,j} g_j(x, y, z).$$

37. A computer-readable medium containing computer-executable instructions for use in performing a method of magnetic tracking in a tracking volume in the presence of movable magnetic-field distorter, said computer-executable instructions comprising:
  a first set of computer-executable instructions for obtaining first magnetic-field data regarding the magnetic field via the magnetic-field sensor while the magnetic-field sensor is in the tracking volume;
  a second set of computer-executable instructions for calculating position and orientation of the magnetic-field sensor as a function of the first magnetic-field data and a difference between a first set of data items and a second set of data items, wherein the first set of data items results from second magnetic-field data collected from the tracking volume when the movable magnetic-field distorter is present in the tracking volume, and the second set of data items results from third magnetic-field data collected from the tracking volume when the movable magnetic-field distorter is not present in the tracking volume; and
  a third set of computer-executable instructions for outputting from a machine information that is a function of the position and orientation of the magnetic-field sensor.

38. A computer-readable medium according to claim 37, wherein the data items of the first and second sets are position and orientation solutions calculated using a position-and-orientation algorithm.

39. A computer-readable medium according to claim 38, further comprising computer-executable instructions for manipulating algorithmically the position and orientation solutions.

40. A computer-readable medium according to claim 37, wherein the data items of the first and second sets are magnetic-field measurements.

41. A computer-readable medium according to claim 40, further comprising computer-executable instructions for manipulating algorithmically the magnetic-field measurements.

42. A computer-readable medium according to claim 37, further comprising computer-executable instructions for interpolating the first and second sets of data items.

43. A computer-readable medium according to claim 37, wherein said computer-executable instructions for calculating of position and orientation include computer-executable instructions for:
  rotating the first magnetic-field data by a matrix A0 to obtain rotated first magnetic-field data having zero orientation;
  rotating the second magnetic-field data by a matrix Ac to obtain zero orientation;
  backing out a range R0 from the rotated first magnetic-field data;
  backing out a range Rc from the rotated second magnetic-field data;
  obtaining matrix components V0 from range R0;
  obtaining matrix components Vc from range Rc;
  determining a difference matrix dV between matrix components V0 and Vc;
  collecting, via the magnetic-field sensor, real-time sensor field data;
  obtaining matrix V from the real-time sensor data;
  obtaining rebuilt sensor field data by incorporating the difference matrix dV into matrix V;
  multiplying the rebuilt sensor field data by $A0^t Ac^t$ so as to obtain a corrected matrix;
  calculating corrected position and orientation data for the magnetic-field sensor as a function of the corrected matrix; and
  outputting from the machine information that is a function of the corrected position and orientation data.

44. A computer-readable medium according to claim 37, wherein said computer-executable instructions for calculating of position and orientation include computer-executable instructions for:
  determining, via the magnetic-field sensor with the magnetic-field distorter present in the tracking volume, position and orientation data R1 regarding the magnetic-field sensor at a particular location within the tracking volume;
  determining, via the magnetic-field sensor with the magnetic-field distorter removed from the tracking volume, position and orientation data S1 regarding the magnetic-field sensor at the particular location;
  calculating a best-fit transformation matrix T that converts S1 into R1;
  collecting, via the magnetic-field sensor, real-time position and orientation data for location within the tracking volume;
  applying the best-fit transformation matrix T to the real-time position and orientation data so as to obtain corrected position and orientation data; and
  outputting from the machine information that is a function of the corrected position and orientation data.

45. A computer-readable medium according to claim 37, wherein said computer-executable instructions for calculating of position and orientation include computer-executable instructions for:
  determining, via at least one magnetic-field sensor with the magnetic-field distorter present in the tracking volume, position and orientation data sets R1 . . . Rn corresponding to differing locations of the at least one magnetic-field sensor within the tracking volume;
  determining, via the at least one magnetic-field sensor with the magnetic-field distorter removed from the tracking volume, position and orientation data sets S1 . . . Sn corresponding to the differing locations;
  calculating a best-fit transformation matrices T1 . . . Tn that convert corresponding respective ones of R1 . . . Rn into corresponding respective ones of S1 . . . Sn;
  forming an interpolation function ƒ from best-fit transformation matrices T1 . . . Tn;

collecting, via the at least one magnetic-field sensor, real-time position and orientation data;
applying the interpolation function $f$ to the real-time position and orientation data so as to obtain corrected position and orientation data; and
outputting from the machine information that is a function of the corrected position and orientation data.

46. A computer-readable medium according to claim 37, wherein said computer-executable instructions for calculating of position and orientation include computer-executable instructions for:
(a) collecting, with the magnetic-field distorter at a known distorter location within the tracking volume, measured magnetic-field data from one or more sensors placed at known sensor locations and orientations within the tracking volume;
(b) calculating expected magnetic-field data expected at each of the known sensor positions and orientations;
(c) determining a difference dF between the measured magnetic-field data and the expected magnetic-field data;
(d) fitting the difference dF and the measured positions and orientations to a dipole model so as to determine dipole parameters;
(e) calculating a magnetic-field contribution M from the dipole model;
(f) determining if |M−dF| is less than a tolerance; and
(g) if |M−dF| is less than the tolerance, save the dipole parameters.

47. A computer-readable medium according to claim 46, further comprising computer-executable instructions for, if |M−dF| is not less than the tolerance:
(h) calculating a new dF=M−dF;
(i) repeating steps (d) through (h) using the new dF until |M−dF| is less than the tolerance.

48. A computer-readable medium according to claim 47, further comprising computer-executable instructions for repeating steps (a) through (i) multiple times for differing distorter locations.

49. A computer-readable medium according to claim 46, further comprising computer-executable instructions for:
(j) collecting real-time magnetic-field data S3 from the at least one magnetic-field sensor;
(k) obtaining real-time distorter location and orientation parameters;
(l) determining a dipole contribution D as a function of the real-time distorter location and orientation parameters;
(m) calculating corrected real-time magnetic-field data as a function of the real-time magnetic-field data S3 and the dipole contribution D;
(n) calculating corrected position and orientation using the corrected real-time magnetic-field data; and
(o) outputting from the machine information that is a function of the corrected position and orientation data.

50. A computer-readable medium according to claim 49, further comprising computer-executable instructions for, prior to step (o):
(p) determining if the corrected position and orientation data has settled and/or if the corrected real-time magnetic-field data has settled;
(q) if one, the other, or both, of the corrected position and orientation data has not settled and/or if the corrected real-time magnetic-field data has settled, repeating steps (l) through (n) and (p); and
(r) if one, the other, or both, of the corrected position and orientation data has settled and/or if the corrected real-time magnetic-field data has settled, proceeding to step (o).

51. A computer-readable medium according to claim 37, wherein said computer-executable instructions for calculating of position and orientation include computer-executable instructions for:
measuring first magnetic-field components within the tracking volume without the magnetic-field distorter present in the tracking volume;
extracting scalar magnetic potentials $g_j$, from the first magnetic-field components;
measuring second magnetic-field components within the tracking volume with the magnetic-field distorter present in the tracking volume;
extracting induced moments $p_k$ from the second magnetic-field components;
determining gradient and scattering matrices $S_{k,j}$ from the scalar magnetic potentials $g_j$, and the induced moments $p_k$;
determine a distorter position and orientation of the magnetic-field distorter;
evaluating and rotating the gradient and scattering matrices as a function of the distorter position and orientation so as to obtain rotated gradient and scattering matrices;
computing multipole moments as a function of the rotated gradient and scattering matrices;
calculating a scattered field as a function of the multipole moments; and
transforming the scattered field to a desired coordinate frame so as to obtain transformed scattered field.

52. A computer-readable medium according to claim 51, further comprising computer-executable instructions for:
(a) collecting real-time magnetic-field data from the magnetic-field sensor;
(b) summing the real-time magnetic-field data with a magnetic-field corrections so as to obtain corrected magnetic-field data;
(c) determining corrected real-time position and orientation data as a function of the corrected magnetic-field data;
(d) outputting information as a function of the corrected real-time position and orientation data;
(e) determining the magnetic-field corrections as a function of the transformed scattered field and the corrected real-time position and orientation data; and
(f) repeating steps (a) through (e).

53. A computer-readable medium according to claim 52, further comprising computer-executable instructions for low-pass filtering the magnetic-field corrections prior to step (b).

54. A computer-readable medium according to claim 51, wherein said computer-executable instructions for determining of the gradient and scattering matrices $s_{k,j}$ from the scalar magnetic potentials $g_j$, and the induced moments $p_k$ include computer-executable instructions for solving the following equation for $s_{k,j}$:

$$p_k = \sum_{j=1}^{J} s_{k,j} g_j(x, y, z).$$

* * * * *